United States Patent [19]
Nicolaou et al.

[11] Patent Number: 5,760,240
[45] Date of Patent: Jun. 2, 1998

[54] TAXOID SYNTHESIS

[75] Inventors: K. C. Nicolaou, La Jolla; Christopher F. Claiborne; Philippe G. Nantermet, both of San Diego; Elias A. Couladouros; Erik J. Sorenson, both of La Jolla, all of Calif.

[73] Assignee: The Scripps Research Institute, La Jolla, Calif.

[21] Appl. No.: 527,377

[22] Filed: Sep. 13, 1995

Related U.S. Application Data

[60] Division of Ser. No. 201,926, Feb. 23, 1994, Pat. No. 5,481,007, which is a continuation-in-part of Ser. No. 197,930, Feb. 16, 1994, abandoned, which is a continuation-in-part of Ser. No. 193,263, Feb. 8, 1994, Pat. No. 5,504,222, which is a continuation-in-part of Ser. No. 110,095, Aug. 20, 1993, Pat. No. 5,440,057, and a continuation-in-part of Ser. No. 141,847, Oct. 22, 1993, abandoned, which is a continuation-in-part of Ser. No. 64,810, May 19, 1993, abandoned, which is a division of Ser. No. 902,390, Jun. 23, 1992, Pat. No. 5,274,137.

[51] Int. Cl.$^6$ .................................................. C07D 213/89
[52] U.S. Cl. ................................................................ 546/347
[58] Field of Search ................................................ 546/347

[56] References Cited

PUBLICATIONS

Masters, et. al., "A Concise Synthesis of a Highly Functionalized C-Aryl Taxol Analog by an Intramolecular Heck Olefination Reaction", *Tet. Letters.*, vol. 34, No. 45, pp. 7253–7256, 1993.

Di Grandi, et. al. "Synthesis of Component Nucleophiles for Delivering the A Ring Of Taxol", *J. Org. Chem.* 58:4989–4992 (1993).

Nicolaou, et. al. "Chemistry and Biology of Taxol", *Angew. Chem. Int. Ed.*, 33: 15–44 (1994).

Nicolaou, et. al. "A Convergent Strategy Towards Taxol. A Facile Enantioselective Entry into a Fully Functionalized Ring A System", *J. Chem. Soc. Chem. Comm.*, 1117–1118, (1992).

Nicolaou, et. al. "Synthesis of a Fully Functionalized CD Ring System of Taxol", *J. Chem. Soc. Chem. Comm.*, 1118–1119, (1992).

Nicolaou, et. al. "Synthesis of ABC Taxoid Ring Systems via a Convergent Strategy", *J. Chem. Soc. Chem. Comm.*, 1024–1025 (1993).

*Primary Examiner*—Ba K. Trinh
*Attorney, Agent, or Firm*—Donald G. Lewis

[57] ABSTRACT

Bioactive ABC taxoids accessible by convergent synthesis have an intact AB ring framework of taxol, including the $C^{13}$ side chain, and an aromatic C ring which substitutes for the CD ring system found on native taxol. The aromatic C ring may be substituted or unsubstituted. MPT derivatives of ABC taxoids are also disclosed.

1 Claim, 5 Drawing Sheets

$R_2 =$ $R_1$ = H, OH, MPT
$R_3$ = H, OH, MPT
$R_4$ = H, OH, MPT

TAXOID SYNTHESIS

CROSS-REFERENCE TO RELATED APPLICATION

The present application is a divisional application of U.S. patent application Ser. No. 08/201,926, filed Feb. 23, 1994, now U.S. Pat. No. 5,481,007 which is a continuation-in-part of U.S. patent application Ser. No. 08/197,930, filed Feb. 16, 1994, now abandoned which is a continuation-in-part of U.S. patent application Ser. No. 08/193,263, filed Feb. 8, 1994, now U.S. Pat. No. 5,504,222 which is a continuation-in-part of U.S. patent application Ser. No. 08/110,095, filed Aug. 20, 1993 now U.S. Pat. No. 5,440,057 and is a continuation-in-part of U.S. patent application Ser. No. 08/141,847, filed Oct. 22, 1993, now abandoned which is a continuation-in-part of U.S. patent application Ser. No. 08/064,810, filed May 19, 1993, now abandoned which is a divisional of U.S. patent application Ser. No. 07/902,390, filed Jun. 23, 1992, now U.S. Pat. No. 5,274,137 the disclosures of which are incorporated herein by reference.

GOVERNMENT RIGHTS

The invention disclosed herein was supported in part by Grant Number CA46446 from the National Institutes of Health. The United States government may have certain rights to this invention.

FIELD OF THE INVENTION

The invention relates to the total synthesis of taxoid molecules and taxoid analogs. More particularly, the invention relates to the synthesis of taxoids and taxoid analogs having an ABC ring skeletal system with an aromatic C ring.

BACKGROUND

Taxol, a substance originally isolated from the Pacific Yew tree (*taxus brevefolia*) has recently been approved for clinical treatment of cancer patients. Recent research efforts directed to its chemical synthesis and the synthesis of taxoid model systems have been recently reviewed by Nicolaou et al., *Angew. Chem. Int. Ed. Engl.* 1994, 33, 15.

A convergent approach to the synthesis of the taxoid family of compounds in which a Shapiro-type coupling is used as a means of joining rings A and C has been disclosed by Nicolaou et al. *J. Chem. Soc., Chem. Commun.* 1993, 1017 and *J. Chem. Soc., Chem. Commun.* 1993, 1118, incorporated herein by reference. This convergent strategy has also been employed by others to accomplish similar couplings, e.g., Di Grandi et al., *J. Org. Chem.* 1993, 58, 4989 and Maskers et al., *Tetrahedron Lett.* 1993, 34, 7253.

When synthesizing complex molecules, convergent strategies are often preferred over linear synthetic schemes because the overall yield can be significant greater for the convergent strategy as compared to linear strategies. This advantage results from the fact the convergent scheme employs multiple starting points and generally fewer steps between each such starting point and the final product.

Although the above convergent strategy for the synthesis of taxol has been shown to be superior to linear schemes, the total length of the scheme remains significant and impairs its value as a commercial route to taxol. What are needed are taxoids and taxoid analogs which share structural and functional similarity with taxol but which are more readily accessible by convergent synthesis.

SUMMARY

The invention is directed advanced taxoid systems accessible by convergent synthesis. More particularly, the invention is directed to a convergent synthetic plan for synthesizing advanced taxoid systems containing the intact AB ring framework of taxol, including the $C^{13}$ side chain, and in which the CD ring system is replaced by an aromatic moiety. The disclosed taxoids are shown to be bioactive. The invention is also directed to MPT derivatives of such taxoids which display enhanced water solubility.

DETAILED DESCRIPTION

According to the convergent strategy, compound 9 (Scheme 1) was targeted as the initial key precursor to the designed molecules. Its construction is outlined in Scheme 1. Hydrazone 2 was coupled with aldehyde 3 leading to racemic 4 in 86% yield according to the method disclosed by Nicolaou et al., *Chem. Soc., Chem. Commun.* 1993, 1024, incorporated herein by reference. Directed epoxidation of 4 using a protocol disclosed by Sharpless et al. (*Aldrichim. Acta* 1979, 12, 63.) gave hydroxy epoxide 5 in 90% yield. Regioselective opening of the oxirane ring in 5 using LiAlH$_4$ was accompanied by desilylation, leading to the corresponding tetraol which was selectively silylated with tert-butyldimethylsilyl chloride, furnishing diol 6 in 75% overall yield. The molecular framework of the intermediates was then rigidified in preparation for the ring closure by carbonate formation through exposure to carbonyl diimidazole (95%) affording compound 7, which was then desilylated and oxidized according to the method of Griffith et al., (*Aldrichim. Acta* 1990, 23, 13) to give dialdehyde 8 (89% overall yield). McMurry coupling (*Chem. Rev.* 1989, 89, 1513; *J. Org. Chem.* 1989, 54, 3748; *Tetrahedron Lett.* 1989, 30, 1169; and *J. Am. Chem. Soc.* 1986, 108, 3513) of the aldehyde groups in 8 produced compound 9 in 53% yield, together with a mixture of three other isomeric diols of gross structure 9 (ca. 20% total yield) and product 9, resulting from a 1,4-participation of the enone functionality in 8 (15% yield). The major isomer 9, m.p. 251° C. (decomp.) (methylene chloride-hexane), was subjected to X-ray crystallographic analysis, revealing the indicated stereochemistry.

Carbonate 9 reacted with excess PhLi at low temperature to form, in a remarkably clean and regioselective fashion, the secondary benzoate 10 in 80% yield (Scheme 2). The later compound was selectivity and quantitatively acetylated by exposure to Ac$_2$O—Et$_3$N, furnishing the corresponding diacetate, which was then oxidized with PCC-NaOAc-celite to enone 11 (55% yield). Reduction of enone 11 with NaBH$_4$ in methanol resulted in the formation of two isomeric alcohols in ca 8:1 ratio and 90% total yield. The two isomers were separated chromatographically (silica, benzene: EtOAc mixtures) leading to pure isomers 12 and 12 (12: major, Rf=0.4; 12: minor, Rf=0.35).

The major compound (12) was assigned the indicated α-stereochemistry on the basis of NMR spectroscopic data. The indicated assignments were made on the basis of the following observations. 12 (major isomer): Irradiation at δ 1.09 (16-CH$_3$) resulted in 20% NOE enhancement at δ 5.81 (9-H), suggesting that 12 adopts a conformation wherein the 16-CH$_3$ and the 9-H are in close proximity as shown below. Irradiation at d 1.03 (17-CH$_3$) resulted in 14.5% NOE enhancement at d 4.33 (13-H), suggesting a β orientation for 13-H as indicated. 12 (minor isomer): Irradiation at δ 1.0 (16-CH$_3$) resulted in 19% NOE enhancement at δ 5.73 (9-H), supporting the conformation shown. Irradiation at δ 1.25 (17-CH$_3$) resulted in no NOE with 13-H as expected for 12.

Attachment of the taxol side chain onto the α-isomer 12 was accomplished using the method disclosed by Holton and Ojima (Holton, R. A. *Eur. Pat. Appl.* EP 400,971, 1990 and *Chem. Abstr.* 1990, 114, 164568q; Ojima et al. *Tetrahedron Lett.* 1993, 34, 4149 and *Tetrahedron* 1992, 48, 6985). Reaction of 12 with β-lactam 13 at −78° C. in the presence of NaN(SiMe$_3$)$_2$ resulted in the formation of two diastereoisomers 14 (Rf=0.45, silica, 80% ether in petroleum ether; $[\alpha]_D^{22}$=+26.67, c 1.5, CHCl$_3$) and 14 (Rf=0.32, silica, 80% ether in petroleum ether; $[\alpha]_D^{22}$=−24.43, c 1.4, CHCl$_3$) in a combined yield of 73% (ca. 1:1 ratio) at ca. 90% conversion. Chromatographic separation of the two diastereoisomers, followed by desilylation resulted in the formation of taxoid 15 (Rf=0.43, silica, ether; $[\alpha]_D^{22}$=+52.33 c 0.3, CHCl$_3$) and its diastereoisomer 15 (Rf=0.32, silica, ether; $[\alpha]_D^{22}$=−16.00 c 0.5, CHCl$_3$) in 90% yield. In order to secure stereochemical assignments, diol 9 was resolved through its diastereomeric dicamphanyl esters 16a and 16b which were separated chromatographically (16a: Rf=0.58, silica, 15% EtOAc in benzene, 16b: Rf=0.50, silica, 15% EtOAc in benzene) according to the method of Gerlach (*Helvetica Chemica Acta* 1978, 61, 2773). The less polar isomer (16a) was hydrolyzed under basic conditions to afford optically active diol 9 ($[\alpha]_D^{22}$ +92.00, c=0.4, CHCl$_3$) whose X-ray crystallographic analysis (see ORTEP drawing, FIG. 1) confirmed its absolute stereochemistry. This diol was then taken through the described sequence to enantiomerically pure 14.

Interestingly, compound 15 exhibited significant cytotoxicity against a variety of tumor cell lines, whereas its diastereoisomer (15') showed essentially no cytotoxicity under the same conditions. Comparative IC$_{50}$ M values for compound 15 and taxol with respect a variety of tumor cell lines is provides below:

| Cell line | IC$_{50}$ M value for compound 15 | IC$_{50}$ M value for Taxol |
|---|---|---|
| HT-29 | 1.29 × 10$^{-7}$ | 5.1 × 10$^{-8}$ |
| Ovcar 3 | 2.80 × 10$^{-7}$ | 6.2 × 10$^{-10}$ |
| UCLA-P3 | 2.96 × 10$^{-7}$ | 6.4 × 10$^{-9}$ |
| A-549 | 6.45 × 10$^{-7}$ | 1 × 10$^{-12}$ |
| L-1210 | 1.11 × 10$^{-6}$ | 7.0 × 10$^{-9}$ |
| SIH-A | 1.29 × 10$^{-6}$ | 1 × 10$^{-12}$ |
| 786-0 | 1.93 × 10$^{-6}$ | 2.2 × 10$^{-6}$ |
| SK-Mel-28 | 2.71 × 10$^{-6}$ | 1.2 × 10$^{-7}$ |
| SK-NH-SH | 4.91 × 10$^{-6}$ | 6.2 × 10$^{-10}$ |
| BT-549 | 5.30 × 10$^{-6}$ | 5.0 × 10$^{-10}$ |

The above results define further structural parameters for the design of bioactive taxoids and provide a synthetic entry to such compounds.

EXAMPLE I: SYNTHESIS OF TAXOL

Production of a preferred activated C ring intermediate, i.e., compound 3

Compound 3 is prepared from common starting materials in three steps.

Step A. One equivalent of pthalic anhydride is reacted with 4 equivalents of LiAlH$_4$ in Et$_2$O at 25° C. for 4 hours. The resulting diol is obtained in 80% yield.

Step B. The diol is then reacted with 0.7 equivalents of $^t$BuPhSi chloride and imidazole in CH$_2$Cl$_2$ at 25° C. for 4 hours in 65% yield.

Step C. The silyl ether is then oxidized with 1.5 equivalents of PCC in CH$_2$Cl$_2$ at 25° C. for 1 hour in 90% yield. Compound 3 is purified by silica gel flash chromatography, Rf=0.40 in 20% Et$_2$O/petroleum ether.

An outline of the synthetic plan for producing compound 3 is illustrated in Scheme 1:

Scheme 1

Production of a preferred activated A ring intermediate, i.e., compound 2

Figure 1:
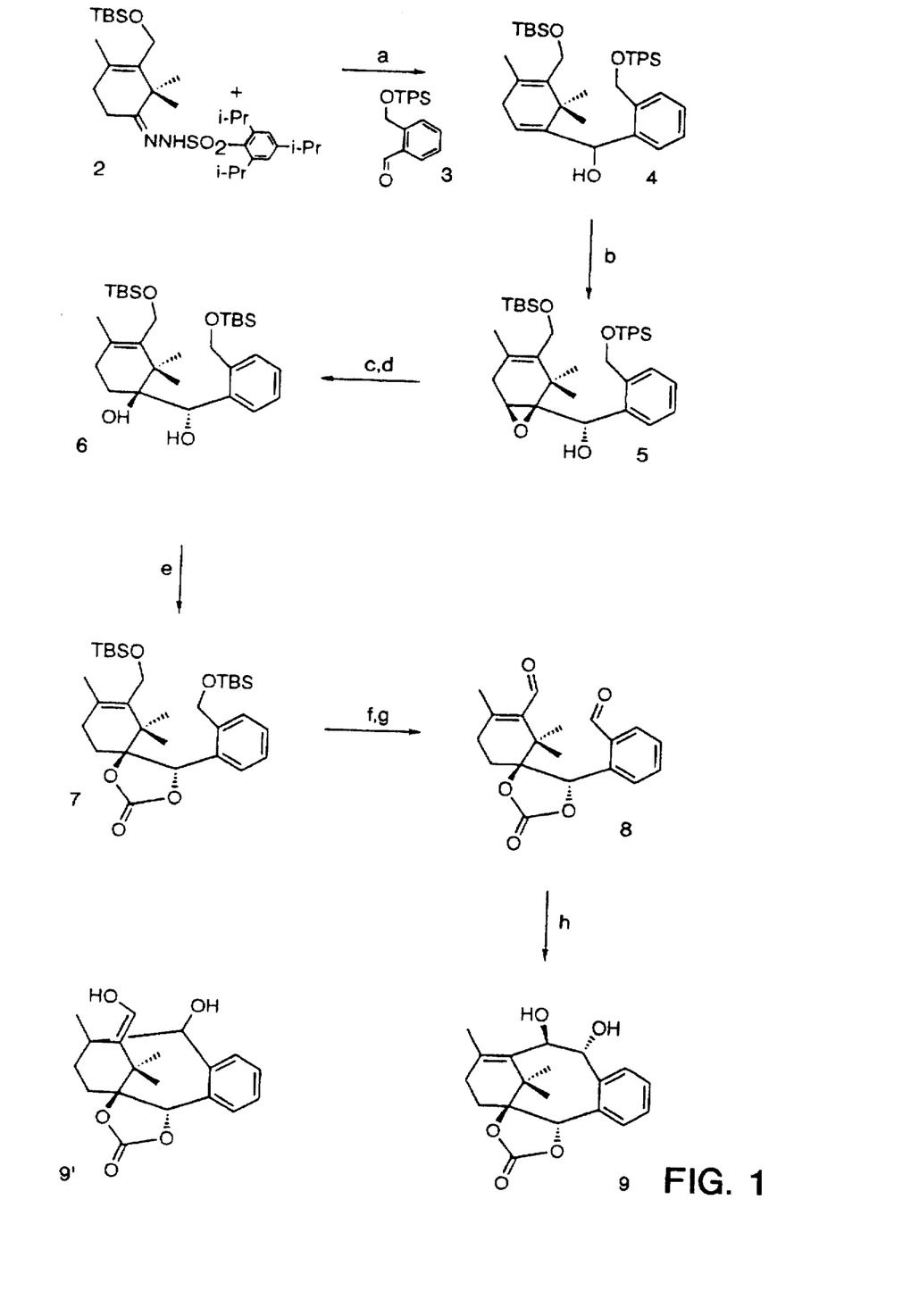
FIG. 1 illustrates a preferred route for the synthesis of key intermediate 9.

A preferred embodiment of the activated A ring intermediate is illustrated as compound 2 in FIG. 1. A synthetic plan for producing compound 2 using simple commercially available starting materials is disclosed in detail by Nicolaou, K. C., Hwuang, C.-K., Sorensen, E. J., and Clairborne, C. F., (1992), *J. Chem. Soc. Chem. Commun.*, Issue 16: 1117. An outline of Nicolaou's synthetic plan for producing compound 2 is illustrated in Scheme 2:

Scheme 2

Briefly, heating of the diene A with 1.5 equivalents of 2-chloroacrylonitrile B for 96 hours at 135° C. in a sealed tube resulted in the formation of intermediate C in 85% yield. Intermediate C is purified by silica gel flash chromatography, Rf=0.25 in 10% Et$_2$O/petroleum ether. Generation of the carbonyl group from the chloronitrile C under basic conditions (5 equivalents of KOH in 'butanol, at 70° C. for 4 hours, afforded the corresponding hydroxyketone in 90% yield which was reacetylated under standard conditions (1.3 equivalents of Ac$_2$O, 1.3 equivalents of 4-dimethylaminopyridine in CH$_2$Cl$_2$ at 25° C. for 1 hour) leading to the ketoacetate D in 98% yield, where "X" represents the keto group. The ketoacetate D is converted to the hydroxy ketone under basic conditions under standard procedures and was subsequently protected as its methoxyethyl methyl ether by reacting 1.0 equivalent of the hydroxy ketone of D with 1.3 equivalents of Pr$^i$2EtN, 1.2 equivalents of methoxyethyl methyl chloride in CH$_2$Cl$_2$ at 25° C. for 3 hours (yield is 95%). The methoxyethyl methyl ether of D is converted to compound 8 in a reaction with 1.0 equivalent of 2,4,6-triisopropylbenzene sulfonylhydrazide in MeOH at 25° C. for 4 hours (yield is 70%), Nicoloaou, K. C., Yang, Z., Sorensen, E. J., and Nakada, M. (1993) *J. Chem. Soc. Chem. Commun.* Issue 12: 1024. The linkage oxygen on the acetate group of diene A corresponds, after many intervening synthetic steps, to the oxygenation found on the tricyclic ABC ring skeleton at position $C^{10}$ of taxoid 15.

Production of a preferred bicyclic AC ring intermediate, i.e., Compound 4

A preferred embodiment of the bicyclic AC ring intermediate is illustratred as compound 4 in FIG. 1. Compound 4 is synthesized by combining the activated A ring intermediate (compound 2) with the activated B ring intermediate (compound 2) in one step.

Step A. One equivalent of compound 2 is combined with 2.1 equivalents of $^n$BuLi in THF at −78° C., the solution is allowed warm to 25° C., and then cooled to 0° C., to which 1.1 equivalents of compound 3 in THF is added. Reaction is allowed to proceed for 0.5 hour. Compound 4 (final yield=86%) is purified by silica gel flash chromatography, Rf=0.25 in 20% EtOAc/petroleum ether.

Physical data for compound 4; The numbering in the following compounds is based on the taxol numbering.

4: White foam; R$_f$=0.25 (silica, 20% EtOAc in petroleum ether); IR (film) n$_{max}$ 3345, 2956, 1472, 1428 cm$^{-1}$; $^1$H NMR (CDCl$_3$) d 7.87–7.78 (m, 4H, Ar), 7.68 (m, 1H, Ar), 7.55–7.32 (m, 9H, Ar), 5.92 (X of ABX, dd, J=3.0, 3.5 Hz, 1H, 14-H), 5.69 (s, 1H, 2-H), 5.04 (A of AB, dd, J=13.0 Hz, 1H, CH$_2$OTBS), 4.79 (B of AB, d, J=13.0 Hz, 1H, CH$_2$OTBS), 4.28 (s, 2H, CH$_2$OTPS), 2.96 (s, 1H, OH), 2.81 (A of ABX, dd, J=3.0, 23.0 Hz, 1H, 13-H), 2.74 (B of ABX, dd, J=3.5, 23.0 Hz, 1H, 13-H), 1.87 (s, 3H, 18-CH$_3$), 1.40 (s, 3H, 17-CH$_3$), 1.20 (s, 9H, tBu), 1.01 (s, 9H, tBu), 0.92 (s, 3H, 16-CH$_3$), 0.19 (s, 3H, Me of TBS), 0.18 (s, 3H, Me of TBS); $^{13}$C NMR (125 MHz, CDCl$_3$) d 143.9, 141.6, 137.3, 135.6, 135.5, 132.9, 132.8, 129.8, 129.7, 129.0, 128.2, 127.8, 127.7, 127.5, 127.4, 127.3, 69.09, 64.52, 58.77, 38.25, 33.37, 27.89, 27.85, 26.77, 26.34, 25.95, 19.10, 18.29, −5.38; HRMS (FAB) Calcd for C$_{40}$H$_{56}$O$_3$Si$_2$ (M+Cs$^+$): 773.2822, found 773.2824.

Production of a preferred activated bicyclic AC ring intermediate, i.e., Compound 8

A preferred embodiment of the activated bicyclic AC ring intermediate is illustratred as compound 8 in FIG. 1. Compound 8 is synthesized from the unactivated bicyclic AC ring intermediate (compound 4) via intermediates 5, 6 and, 7.

Compound 5 is synthesized from compound 4 in one step.

Step B. Compound 4 is allowed to react with 0.05 equivalents of VO(acac)$_2$, 1.5 equivalents of $^t$BuOOH in benzene at 25° C. for 5 hours. Compound 5 (final yield=90%) is purified by silica gel flash chromatography, Rf=0.30 in 20% Et$_2$O/petroleum ether. The ring oxygen within the resultant epoxide of compound 5 corresponds, after many intervening synthetic steps, to the oxygenation found on the tricyclic ABC ring skeleton at position $C^1$.

Physical data for compound 5

5: White foam; R$_f$=0.30 (silica, 20% ether/petroleum ether); IR (film) n$_{max}$ 3385, 2955.4, 1471, 1427, 1253 cm$^{-1}$; $^1$H NMR (500 MHz, CDCl$_3$) d 7.70 (d, J=7.0, Hz, 2H, Ar), 7.54

(d, J=7.0 Hz, 1H, Ar), 7.46–7.23 (m, 11H, Ar), 5.28 (s, 1H, 2-H), 4.90 (A of AB, d, J=13.5 Hz, 1H, CH$_2$OTPS), 4.84 (B of AB, d, J=13.5 Hz, 1H, CH$_2$OTPS), 4.12 (A of AB, d, J=11.0 Hz, 1H, CH$_2$OTPS), 3.09 (s, 1H, 14-H), 2.76 (broad s, 1H, OH), 2.41 (A of AB, d, J=19.0 Hz, 13-H), 2.36 (B of AB, d, J=19.0 Hz, 13-H), 1.67 (s, 3H, 18-CH$_3$), 1.29 (s, 3H, 16- or 17-CH$_3$), 1.11 (s, 9H, tBu), 0.88 (s, 9H, tBu), 0.81 (s, 3H, 16- or 17-CH$_3$), 0.05 (s, 6H, Me$_2$ of TBS); $^{13}$C NMR (125 MHz, CDCl$_3$) d 138.2, 137.7, 135.6, 135.5, 133.8, 133.1, 133.0, 129.7, 127.9, 127.7, 127.2, 127.0, 126.3, 124.9, 66.2, 66.1, 63.4, 58.8, 58.1, 38.6, 31.7, 26.7, 25.9, 25.8, 22.0, 19.6, 19.23, 18.2, −5.5, −5.6; HRMS (FAB) Calcd for C$_{40}$H$_{56}$Si$_2$O$_4$ (M+Cs$^+$): 789.2772, found 789.2775.

Compound 6 is synthesized from compound 5 in two steps.

Steps C and D. Compound 5 is allowed to react with 5 equivalents of LiAlH$_4$ in Et$_2$O under reflux for 7 hours. The resulting crude tetra-ol is then reacted with 2.1 equivalents of $^t$BuMe$_2$Si chloride, 2.5 equivalents of imidazole in CH$_2$Cl$_2$ at 25° C. for 1 hour. Compound 6 (final yield=75%) is purified by silica gel flash chromatography, Rf=0.45 in 20% Et$_2$O/petroleum ether.

Compound 7 is synthesized from compound 6 in one step.

Step E. Compound 6 is allowed to react with 10 equivalents of carbonyl diimidazole, in acetonitrile under reflux for 2 hours. The resultant carbonate 7 is purified by silica gel flash chromatography, Rf=0.6 in 20% Et$_2$O/petroleum ether.

Compound 8 is synthesized from compound 7 in two steps

Step F. The carbonate is allowed to react with 4 equivalents of tetra-n-buylammonium fluoride in THF at 25° C. for 2 hours.

Step G. The resultant crude diol is allowed to react with 0.05 equivalents of tetra-n-propylamionium perruthourenate, 5 equivalents of 4-methylmorpholine-n-oxide in CH$_2$Cl$_2$ at 25° C. for 2 hour. Compound 8, the dialdehyde (final yield=89%), is purified by silica gel flash chromatography, Rf=0.60 in 60% EtOAc/ petroleum ether.

Physical data for compound 8.

8: White solid mp 162 C; R$_f$=0.6 (silica, 60% EtOAc in petroleum ether); IR (film) n$_{max}$ 2978, 1798.4, 1701.1, 1671.4 cm$^{-1}$; $^1$H NMR (CDCl$_3$) d 10.08 (s 1H, CHO), 10.04 (s, 1H, CHO), 7.87 (dd, J=1.5, 7.6 Hz, 1H, Ar), 7.72 (m, 1H, Ar), 7.66 (m, 1H, Ar), 7.51 (d, J=7.8 Hz, 1H, Ar), 6.81 (s, 1H, 2-H), 2.36 (m, 1H, 13-H), 2.02 (s, 3H, 18-CH$_3$), 1.85 (m, 1H, 13-H), 1.52 (s, 3H, 16-CH$_3$), 1.50 (s, 3H, 17-CH$_3$), 1.48 (m, 2H, 14-CH$_2$); $^{13}$C NMR (125 MHz, CDCl$_3$) d 192.41, 191.51, 154.68, 153.55, 137.07, 136.39, 135.47, 134.02, 133.57, 129.73, 128.85, 90.66, 76.27, 41.46, 31.45, 24.51, 23.40, 19.73, 8.51; HRMS (FAB) Calcd for C$_9$H$_{20}$O$_5$ (M+Na$^+$): 351.1205, found 351.1210.

Production of a preferred tricyclic ABC ring intermediate, i.e., Compound 9

Figure 2:
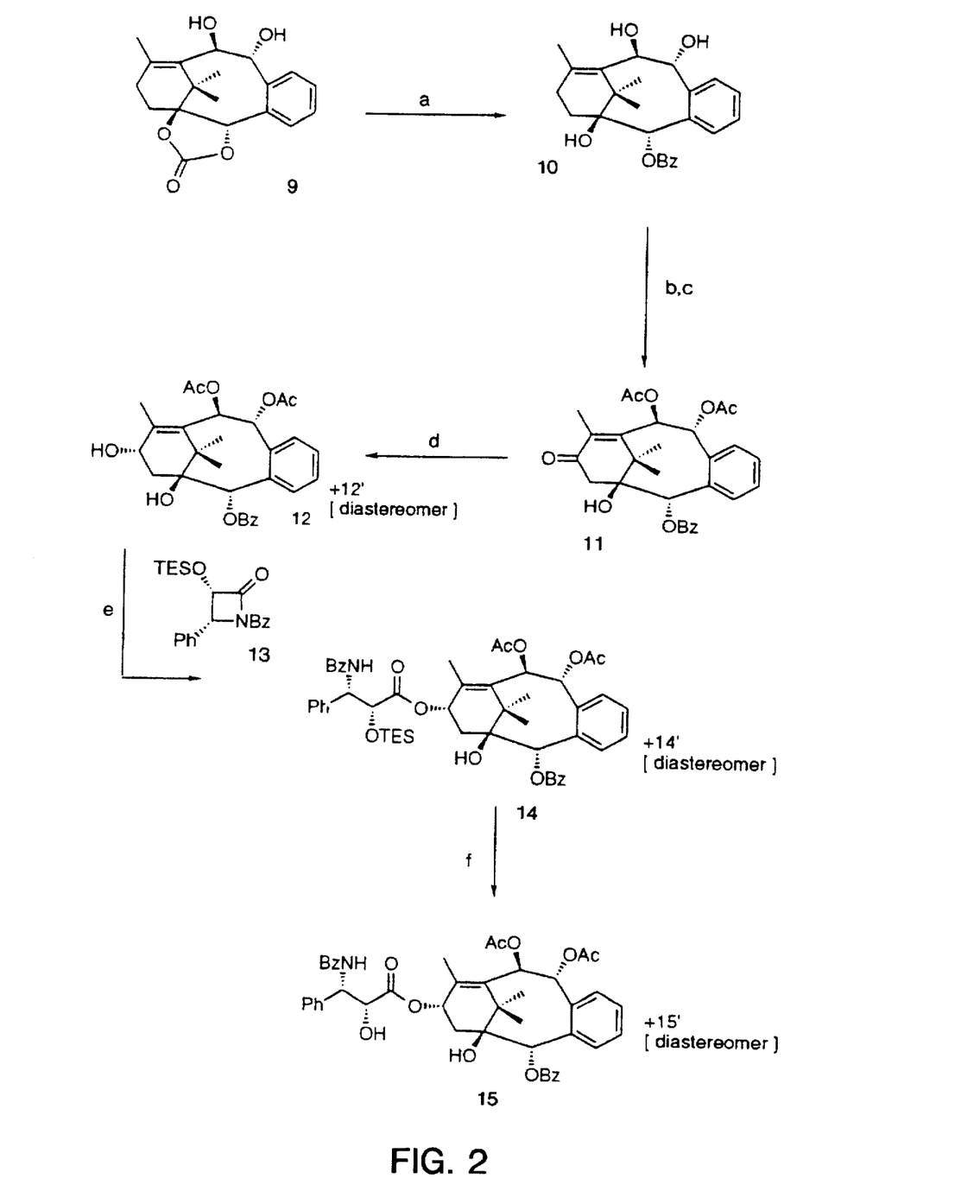
FIG. 2 illustrates a preferred route for the synthesis of compound 15, i.e., a bioactive taxoid having an aromatic C ring.

A preferred embodiment of a tricyclic ABC ring intermediate is illustratred as compound 9 in FIGS. 1 and 2. Compound 9 is synthesized from the activated bicyclic AC ring intermediate (compound 8).

Compound 9 is synthesized from compound 8 in one step.

Step H. Compound 8 is allowed to react with 10 equivalents of (TiCl$_3$)$_2$·(DME)$_3$, 40 equivalents of Zn—Cu in DME under at 55° C. for 3 hour. Compound 9 (final yield=53% plus 20% total of two unassigned stereoisomers, plus 15% of 9', FIG. 1) is purified by silica gel flash chromatography, Rf=0.20 in ether.

Physical data for compound 9

9: White solid mp 251 C (decomposition); R$_f$=0.2 (silica, ether); IR (film) n$_{max}$ 3426, 2936.6, 1799.9, 1457.2, 1026.4 cm$^{-1}$; $^1$H NMR (CD$_3$CO) d 7.82 (m, 1H, Ar), 7.47 (m, 1H, Ar), 7.30 (m, 2H, Ar), 5.91 (s, 1H, 2-H), 5.14 (dd, J=3.0, 8.5 Hz, 10-H or 9-H), 4.83 (d, J=3.0 Hz, 1H, OH), 4.64 (dd, 3=3.0, 8.5 Hz, 1H, 10-H or 9-H), 4.41 (d, J=3.0 Hz, 1H, OH), 2.37 (m, 1H, 13-H), 2.29 (m, 1H, 13-H), 1.89 (m, 1H, 14-H), 1.72 (s, 3H, 18-CH$_3$), 1.19 (m, 1H, 14-H), 1.17 (s, 3H, 16-CH$_3$), 0.79 (3H, 17-CH$_3$); $^{13}$C NMR (125 MHz, CD$_3$CO) d 154.2, 142.0, 138.0, 133.2, 132.9, 128.2, 127.5, 126.4, 124.1, 93.0, 80.3, 79.2, 75.2, 40.6, 29.5, 23.5, 21.5, 21.1; HRMS (FAB) Calcd for C$_{19}$H$_{22}$O$_5$ (M+Na$^+$): 353.1365, found 353.1360.

Production of a preferred C$^{13}$ oxygenated tricyclic ABC ring intermediate, i.e., compound 12

A preferred embodiment of the tricyclic ABC ring skeleton is illustratred as compound 12 in FIG. 2. Compound 12 is synthesized from the activated tricyclic ABC ring intermediate compound 9 via intermediates 10 and 11.

Compound 12 is prepared from compound 9 in four steps, FIG. 2.

Step A. Compound 9 is reacted with 10 equivalents of PhLi in THF at −78° C. for 30 minutes. Compound 10 (final yield equals 96%) is purified by silica flash chromatography, Rf=0.50 in 50% EtOAc/petroleum ether.

Physical data for compound 10

10: Colorless solid; R$_f$=0.5 (silica, 50% ethyl acetate/ petroleum ether); IR (film) n$_{max}$ 3456, 2945, 1704, 1450, 1283 cm$^{-1}$; $^1$H NMR (500 MHz, CDCl$_3$) d 8.05 (m, 1H, Ar), 7.58–7.41 (m, 4H, Ar), 7.15 (m, 2H, Ar), 6.31 (s, 1H, 2-H), 5.41 (d, J=9.0 Hz, 1H, 10-H), 4.50 (d, J=9.0 Hz, 1H, 9-H), 2.41 (m, 1H, 13-H), 2.28 (m, 1H, 13-H), 1.84 (m, 1H, 14-H), 1.73 (s, 3H, 18-CH$_3$), 1.36 (s, 3H, 16- or 17-CH$_3$), 1.15 (s, 3H, 16- or 17-CH$_3$), 0.62 (s, 3H, 16- or 17-CH$_3$); $^{13}$C NMR (125 MHz, CDCl$_3$) d 165.9, 139.6, 138.5, 138.1, 133.2, 131.4, 129.8, 129.5, 128.4, 126.9, 126.5, 124.4, 123.8, 79.7, 79.2, 74.3, 74.1, 41.5, 29.8, 27.2, 26.1, 20.3, 19.6, 14.1; HRMS (FAB) Calcd for C$_{25}$H$_{28}$O$_5$ (M+Na$^+$): 431.1834, found 431.1830.

Figure 3:
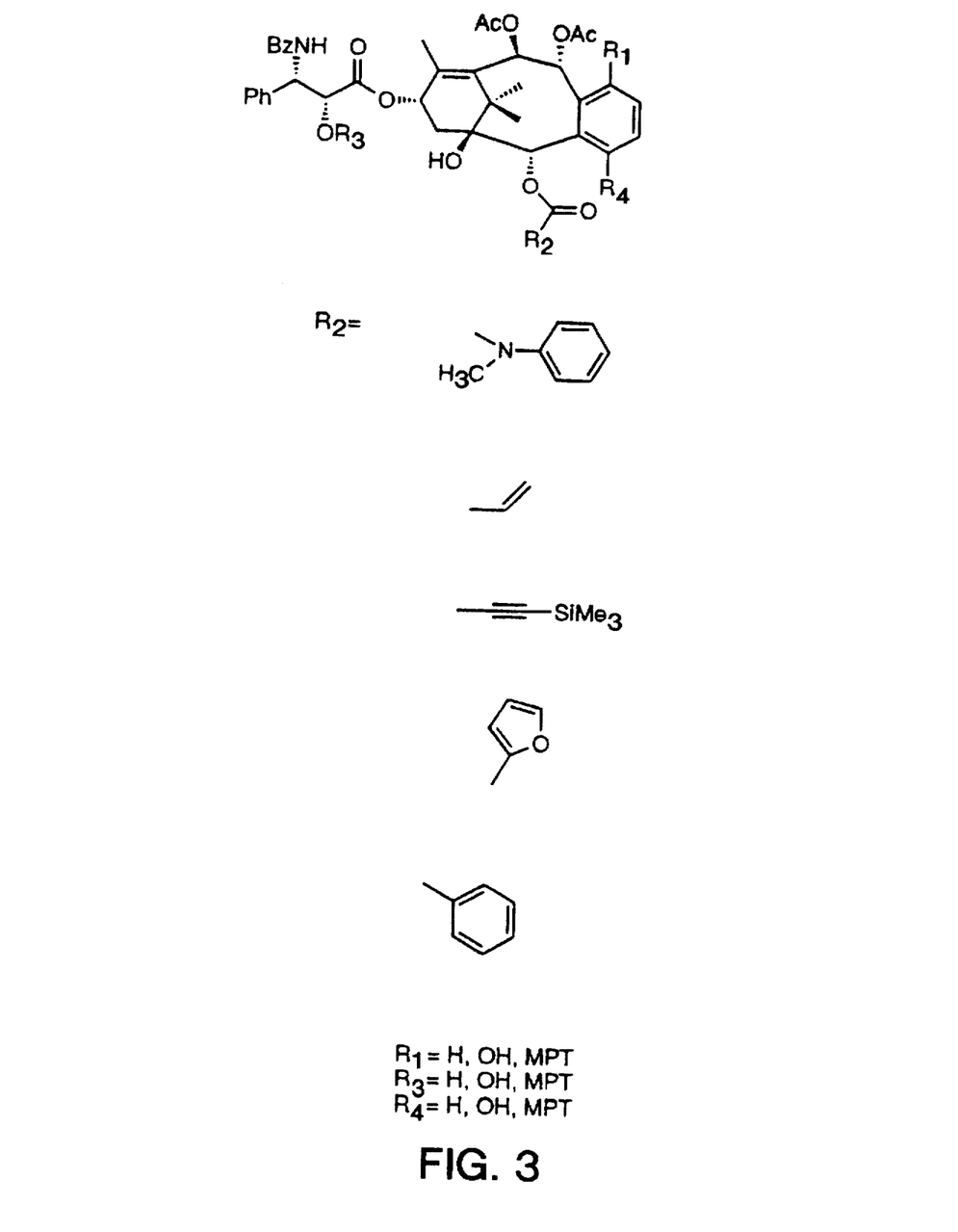
FIG. 3 illustrates taxoids having various substitutions at the $C^2$, $C^{2'}$, $C^4$, and $C^7$ positions.

Alternative Embodiments of Step A. The carbonate ester of 9 can also be removed with other organo-lithium compounds. Such compounds are illustrated in FIG. 3 and yield the corresponding modified derivatives of taxoid 15. In similar fashion to the reaction with PhLi in Step A, compound 9 is reacted with excess organo-lithium in a suitable solvent.

Step B. 10 is reacted with 2.5 equivalents of Ac$_2$O, 2.8 equivalents of Et$_3$N, 0.05 equivalents of 4-N-dimethylaminopyridine in CH$_2$Cl$_2$ at 25° C. for 1 hour.

Step C. The resulting acetylated intermdiate is reacted with 30 equivalents of PCC, celite, and 20 equivalents of NaOAc in benzene under reflux for 2 hours. Compound 11 (final yield equals 55%) is purified by silica gel flash chromatography, Rf=0.50 in 60% EtOAc/ petroleum ether.

Step D. Compound 11 is reacted with 20 equivalents of NaBH$_4$ in MeOH at 0° C. for 20 minutes. Compound 12 (an 8:1 mixture of a and b isomers, final yield equals 90%) is purified by silica gel flash chromatography, Rf=0.40 in 30% EtOAc/petroleum ether.

Physical data for compound 12

12: Colorless solid; R$_f$=0.4 (silica, 30% EtOAc in petroleum ether); IR (film) n$_{max}$ 3509, 2925.7, 1724.3 cm$^{-1}$; $^1$H NMR (CDCl$_3$) d 8.15 (m, 2H, OBz), 7.20–7.70 (m, 7H, Ar), 6.69 (d, J=10.0 Hz, 1H, 10-H), 6.47 (s,1H, 2-H), 5.81 (d, J=10.0

Hz, 1H, 9-H), 4.33 (X of ABX, m, 1H, 13-H), 2.58 (A of ABX, dd, J=10.0, 19.5 Hz, 1H, 14-H), 2.27 (broad s, 1H, OH), 2.42 (B of ABX, dd, J=3.5, 19.5 Hz, 1H, 14-H), 2.21 (s, 3H, OAc), 2.14 (s, 3H, OAc), 1.75 (s, 3H, 18-CH$_3$), 1.09 (s, 3H, 16-CH$_3$), 1.03 (s, 3H, 17-CH$_3$); $^{13}$C NMR (125 MHz, CDCl$_3$) d 170.2, 169.4, 165.5, 142.8, 140.1, 136.5, 133.4, 130.6, 129.6, 129.5, 128.5, 127.8, 127.6, 125.7, 124.1, 77.15, 76.6, 74.05, 71.82, 67.62, 39.7, 29.58, 27.53, 21.02, 20.84, 19.75, 15.29; HRMS (FAB) Calcd for C$_{29}$H$_{32}$O$_8$ (M+H$^+$): 509.2175, found 509.2175.

Production of a molecule having a tricyclic ABC ring skeleton and an oxygenated C$^{13}$, i.e., Compound 15

A preferred embodiment of the tretracyclic ABC ring skeleton with an appended C$^{13}$ ester is illustratred as compound 15, i.e., Taxoid 15. Taxoid 15 is synthesized from the tricyclic ABC ring intermediate (compound 12) via intermediate 14.

Compound 14 is prepared from compound 12 in one step.

Step E. Compound 12 is reacted with 2 equivalents of 13, (Compound 13 is prepared as previously described in Farina, V., Hauck, S. I., and Walker, D. G., (1992) Synlett., 761.), 3 equivalents of NaN(SiMe$_3$)$_2$ in THF at −78° C. for 30 minutes. Compound 14 (final yield equals 33% plus 33% od 14' plus 10% recovered starting material) is purified by silica gel flash chromatography, Rf=0.32 in 80% Et$_2$O/petroleum ether.

Physical data for compounds 14 and 14'14: Colorless solid; R$_f$=0.32 (silica, 80% ether in petroleum ether); IR (film) n$_{max}$ 3421.8, 2955.1, 1746.3, 1663.2, 1025.3 cm$^{-1}$; [a]$^{22}$D=−24.43 (CHCl$_3$); $^1$H NMR (500 MHz, CDCl$_3$) d 8.07 (d, J=7.0 Hz, 2H, Ar), 8.69 (d, J=7.0 Hz, 2H, Ar), 7.75–7.25 (m, 15H, Ar), 7.09 (d, J=8.5 Hz, 1H, NH), 6.67 (d, J=10.0 Hz, 1H, 10-H), 6.46 (s, 1H, 2-H), 5.81 (d, J=10.0Hz, 1H, 9-H), 5.54 (m, 1H, 13-H), 5.18 (d, J=8.5 Hz, 1H, 3-H), 4.37 (d, J=1.5 Hz, 1H, 2-H), 2.61 (s, 1H, tert-OH), 2.56 (dd, J=6.4, 10.3 Hz, 1H, 14-H), 2.30 (dd, J=2.7, 10.3 Hz, 1H, 14-H), 2.20 (s, 3H, OAc), 2.10 (s, 3H, OAc), 1.74 (s, 3H, 18-CH$_3$), 1.05 (s, 3H, 16-CH$_3$), 1.00 (s, 3H, 17-CH$_3$), 0.84 (t, J=8.0 Hz, 9H, SiCH$_2$CH$_3$), 0.47 (m, 6H, SiCH$_2$CH$_3$); $^{13}$C NMR (125 MHz, CDCl$_3$) d 170.4, 170.1, 169.5, 166.5, 165.6, 139.1, 138.9, 138.7, 136.1, 134.2, 133.5, 132.1, 131.6, 129.6, 129.0, 128.7, 128.6, 128.5, 127.7, 127.6, 127.2, 127.0, 126.4, 125.5, 125.3, 76.92, 76.74, 75.28, 74.27, 71.9, 70.63, 55.9, 42.0, 36.6, 27.6, 21.0, 20.9, 19.8, 15.6, 6.5, 4.3; HRMS (FAB) Calcd for C$_{51}$H$_{59}$O$_{11}$NSi (M+Cs$^+$): 1022.2912, found 1022.2935.

14': Colorless solid; R$_f$=0.45 (silica, 80% ether in petroleum ether); [a]$^{22}$D=26.67 (CHCl$_3$); IR (film) n$_{max}$ 3428.6, 3955.6, 1746.9, 1667.5 cm$^{-1}$; $^1$H NMR (500 MHz, CDCl$_3$) d 8.27 (d, J=8.0 Hz, 2H, Ar), 8.13 (d, J=8.0 Hz, 1H, Ar), 7.87 (m, 2H, Ar), 7.60–7.20 (m, 14H, Ar), 7.14 (d, J=9.0 Hz, 1H, NH), 6.73 (d, J=10.0 Hz, 1H, 10-H), 6.43 (s, 1H, 2-H), 5.81 (d, J=10.0 Hz, 2H, 9-H and 3H), 5.64 (m, 1H, 13-H), 4.33 (d, J=2.0 Hz, 1H, 2-H), 2.58 (s, 1H, tert-OH), 2.41 (m, 2H, 14-CH$_3$), 2.20 (s, 3H, OAc), 2.13 (s, 3H, OAc), 1.73 (s, 3H, 18-CH$_3$), 1.07 (s, 3H, 16-CH$_3$), 0.98 (s, 3H, 17-CH$_3$), 0.71 (t, J=8.0 Hz, 9H, SiCH$_2$CH$_3$), 0.3 (m, 6H, SiCH$_2$CH$_3$); $^{13}$C NMR (125 MHz, CDCl$_3$) d 170.4, 170.2, 169.4, 167.0, 165.8, 139.4, 139.1, 138.3, 135.6, 134.8, 133.2, 132.0, 131.7, 130.2, 129.5, 128.8, 128.6, 128.4, 128.0, 127.6, 127.1, 127.05, 127.0, 126.2, 124.6, 77.16, 77.74, 75.13, 74.2, 71.9, 70.40, 55.5, 42.2, 35.8, 27.0, 21.1, 21.0, 20.0, 15.3, 6.4, 4.2; HRMS (FAB) Calcd for C$_{51}$H$_{59}$O$_{11}$NSi (M+Cs$^+$): 1022.2912, found 1022.2930.

Compound 15 is then formed from compound 14
Step F.

Compound 14 is then reacted with 2 equivalents of HF·pyridine in THF at 25° C. for 2 hours to produce compound 15. The resultant taxoid (final yield equals 90%) is purified by silica gel flash chromatography, Rf=0.32 in Et$_2$O.

Physical data for compounds 15 and 15'

15: Colorless solid; R$_f$=0.32 (silica, ether); [a]$^{22}$D=−16.00 (CHCl$_3$); IR (film) n$_{max}$ 3422.9, 2929.2, 1736.5, 1657.5, 1237.1 cm$^{-1}$; $^1$H NMR (500 MHz, CDCl$_3$) d 8.07 (d, J=8.0 Hz, 2H, Ar), 7.69 (d, J=8.0 Hz, 2H, Ar), 7.65–7.20 (band, 15H, Ar), 7.00 (d, J=9.0 Hz, 1H, NH), 6.66 (d, J=10.0 Hz, 1H, 10-H), 6.42 (s, 1H, 2-H), 5.77 (d, J=10.0 Hz, 1H, 9-H), 5.59 (broad d, J=8.0 Hz, 1H, 13-H), 5.33 (dd, J=2.0, 9.0 Hz, 1H, 3-H), 4.50 (dd, J=2.5, 4.0 Hz, 1H, 2-H), 3.16 (d, J=4.0, Hz, 1H, 2-OH), 2.72 (s, 1H, tert-OH), 2.54 (dd, J=10.0, 15.0 Hz, 1H, 14-H), 2.22 (dd, J=3.5, 15.0 Hz, 1H, 14-H), 2.18 (s, 3H, OAc), 2.11 (s, 3H, OAc), 1.73 (s, 3H, 18-CH$_3$), 1.04 (s, 3H, 16-CH$_3$), 0.98 (s, 3H, 17-CH$_3$); $^{13}$C NMR (125 MHz, CDCl$_3$) d 171.55, 170.18, 169.52, 166.56, 165.75, 38.8, 138.7, 137.96, 127.3, 127.0, 126.9, 125.5, 125.2, 76.9, 76.76, 74.17, 73.47, 71.97, 71.85, 54.8, 42.1, 36.41, 27.63, 21.05, 20.95, 19.83, 15.56; HRMS (FAB) Calcd for C$_{45}$H$_{45}$O$_{11}$N (M+Cs$^+$): 908.2047, found 908.2038.

15': Colorless solid; R$_f$=0.43 (silica, ether); [a]$^{22}$D=−24.43 (CHCl$_3$); IR (film) n$_{max}$ 3729.4, 3416.9, 1654.3, 1515.3, 1026.6 cm$^{-1}$; $^1$H NMR (500 MHz, CDCl$_3$) d 8.30 (d, J=8.0 Hz, 2H, Ar), 8.18 (d, J=8.0 Hz, 1H, Ar), 7.84 (d, J=8.0 Hz, 2H, Ar), 7.60–7.20 (m, 14H, Ar), 6.99 (d, J=9.5 Hz, 1H, NH), 6.73 (d, J=10.0 Hz, 1H, 10-H), 6.45 (s, 1H, 2-H), 5.88 (d, J=9.5 Hz, 1H, 3-H), 5.79 (d, J=10.0 Hz, 1H, 9-H), 5.72 (X of ABX, m, 1H, 13-H), 4.47 (s, 1H, 2-H), 3.26 (broad s, 1H, 2-OH), 2.66 (s,1H, tert-OH), 2.61 (A of ABX, dd, J=4.0, 15.5 Hz, 1H, 14-H), 2.38 (B of ABX, dd, J=10.5, 15.5 Hz, 1H, 14-H), 2.20 (s, 3H, OAc), 2.13 (s, 3H, OAc), 1.75 (s, 3H, 18-CH$_3$), 1.05 (s, 3H, 16-CH$_3$), 0.91 (s, 3H, 17-CH$_3$); $^{13}$C NMR (125 MHz, CDCl$_3$) d 172.0, 170.4, 169.4, 166.9, 139.3, 138.9, 137.8, 135.5, 134.4, 133.3, 132.5, 131.9, 130.2, 129.6, 128.9, 128.8, 128.5, 128.5, 127.9, 126.85, 127.2, 127.1, 127.0, 126.6, 124.7, 77.08, 76.69, 74.23, 73.17, 71.86, 71.67, 54.0, 42.4, 35.4, 27.2, 21.1, 20.9, 20.0, 15.18; HRMS (FAB) Calcd for C$_{45}$H$_{45}$O$_{11}$N (M+Cs$^+$): 908.2047, found 908.2058.

EXAMPLE II: SYNTHESIS OF TAXOID ANALOGS

Production of Preferred Taxol Analogs with Appended C Ring

Figure 4:
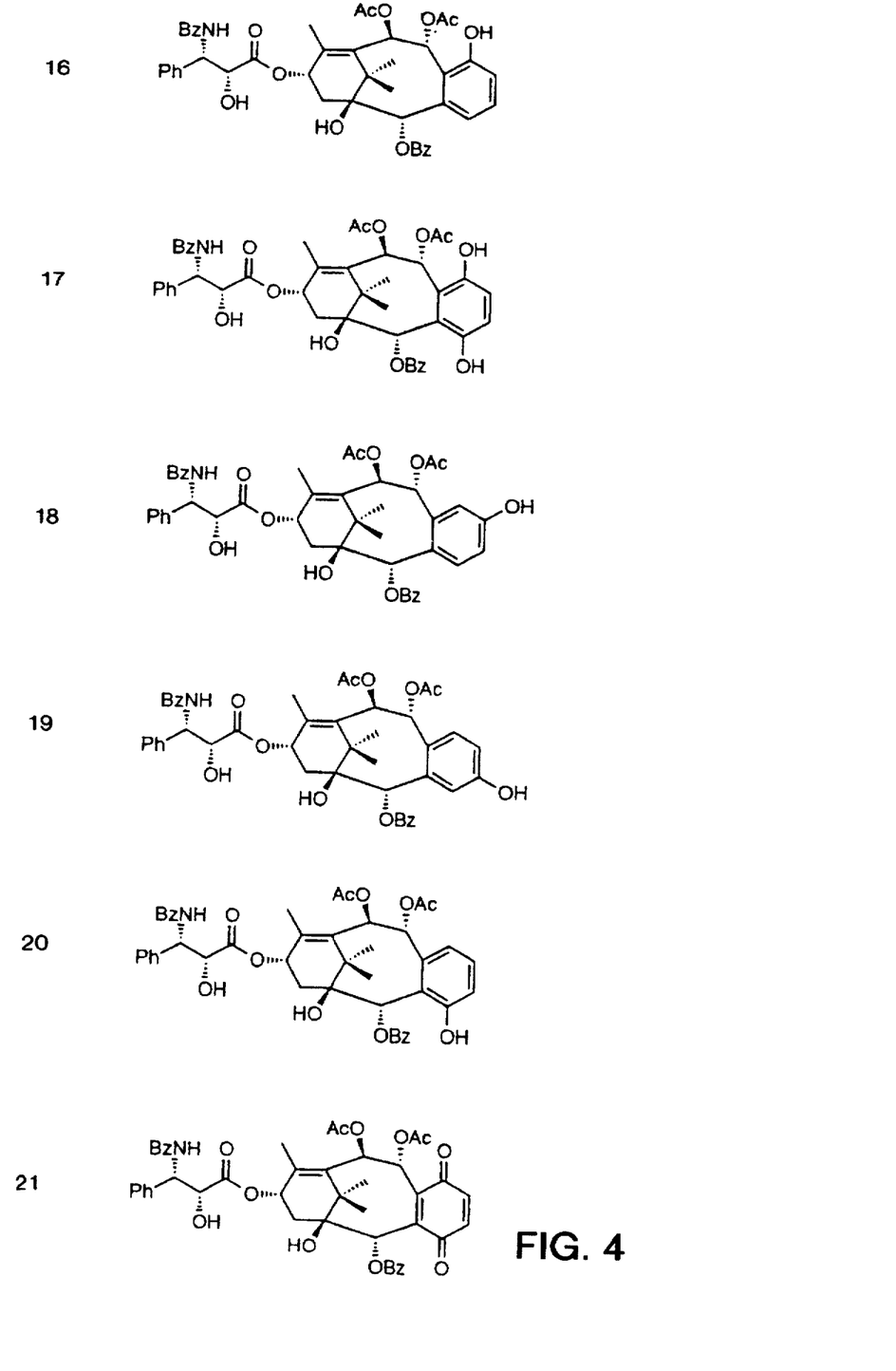
FIG. 4 illustrates alternative taxoids having substituted aromatic C rings.

The synthesis of taxol analogs having a tricyclic ABC ring skeleton with appended skeletal extensions at positions C$^5$, C$^7$, and C$^{19}$ can be carried out with modified compound 3. Scheme 1 illustrates the synthesis of 3. A modified C ring incorporating one, two, three or four hydroxyl groups attached to carbons comprised of C-4, C-5, C-6 or C-7 is readily synthesized from commonly available starting materials ie., 3-hydroxypthalic anhydride, 4-hydroxypthalic anhydride, and 3,4-dihydroxypthalic anhydride. The appropriately protected and modified C ring is then carried through the remaining reactions, as illustrated in FIGS. 1 and 2. Thus, derivatized C-ring starting material will yield the corresponding hydroxylated derivatives of the preferred bicyclic AC ring intermediate 4, as well as the corresponding C-ring derivative of the activated bicyclic AC ring intermediate 8, the C-ring hydroylated derivative intermediate 12, and finally the corresponding C ring-hydroxylated taxoids based on compound 15, ie., compounds 16–21. FIG. 4.

Production of Preferred Taxol Analogs with Sustituents on the A ring

The synthesis of taxol A ring-analogs derivatized in their carbon skeleton at carbons 14, 16, 17 and, 18 (taxol numbering) is carried out with modified compound 2. Synthesis of compound 24 (FIG. 5) follows that of compound 8.

Figure 5:
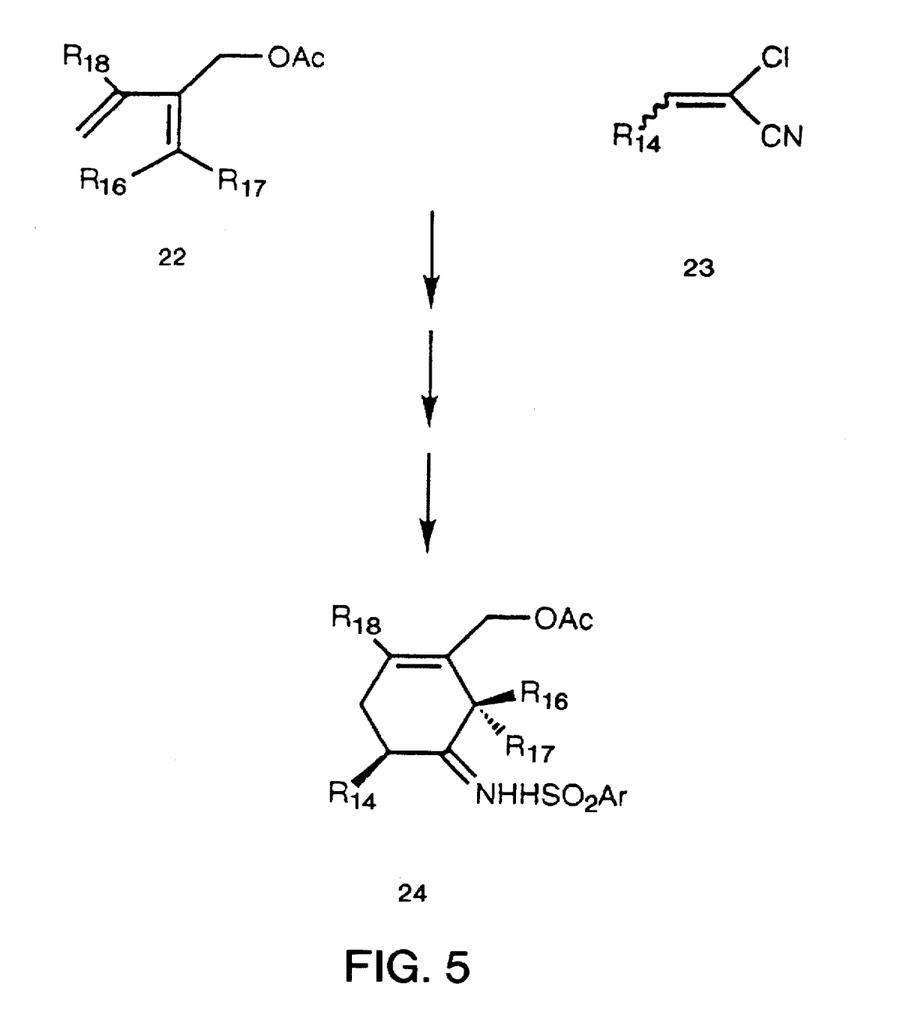
FIG. 5 illustrates reagents employed for synthesizing taxoids having skeletal substitutions or extensions at the $C^{14}$ and $C^{16-18}$ positions.

Nicolaou, K. C., Hwuang, C.-K., Sorensen, E. J., and Claiborne, C. F., (1992), *J. Chem. Soc. Chem. Commun.*, Issue 16: 1117. FIG. 5, the diene 22 is reacted with the 2-chloroacrylonitrile, 23, followed by generation of the carbonyl group from the chloronitrile under basic conditions to afford the corresponding hydroxyketone. The hydroxyketone is reacetylated leading to the ketoacetate, which is converted to the hydroxy ketone, and subsequently protected as its methoxyethyl methyl ether (by reacting the hydroxy ketone with methoxyethyl methyl chloride. The methoxyethyl methyl ether is converted to compound 28 in a reaction with 2,4,6-triisopropylbenzenesulfonylhydrazide. Compound 24 is then carried through the remaining reactions (exemplified in FIGS. 1 and 2) to yield the corresponding A ring-substituted taxoid of 15.

EXAMPLE III: SYNTHESIS OF MPT-TAXOID ANALOGS

Each of the above indicated ABC taxoids and ABC taxoid analogs may be further modified by MPT derivatization according to the method described below for modifying taxol. MPT derivatization enhances the water solubility of such compounds.

Scheme 3A and 3B

Synthesis of Taxol-2'-MPT

Taxol-2'-MPT (methylpyridinium tosylate) was synthesized according to the method of T. Mukaiyama, *Angewandte Chemie* 1979, 18(18), 707–808. Taxol (10 mg, 0.012 mM), from NaPro Biochemicals, Boulder Colo., USA, was dried by azeotropic distillation with toluene (2×1.0 mL) and then dissolved in methylene chloride (0.4 mL) and treated sequentially under an atmosphere of dry argon, with freshly distilled triethylamine (5 microL, 0.04 mM, 3 equivalents) and 2-fluoro-1-methylpyridinium tosylate (5 mg, 0.018 mM, 1.5 equivalents) Aldrich Chemicals, and allowed to stir at ambient temperature for 30 minutes. The clear colorless solution rapidly turned to a clear pale yellow. The course of the reaction was monitored through thin layer chromatography (TLC) (E. Merck RP-18 silica, 65 tetrahydrofuran:35 water, UV/phosphomolybdic acid) and after thirty minutes of stirring at ambient temperature, judged complete as no taxol remained and only one compound was apparent by TLC (Rf 0.8). Purification via reverse phase high pressure liquid chromatography (HPLC) ($C_{18}$ column, 1 mM $NH_4OAc$ pH 6.5 buffer/methanol gradient, 1.5 mL/min, UV) to give, after removal of solvent in vaccuo, pure taxol-2'-MPT (2) (12 mg, 93% yield) as a white amorphous solid. All spectroscopic data ($^1H$ NMR and HRMS) were in accord with the structure assigned to taxol-2'-MPT. $^1H$ NMR ($CDCl_3$, 125 MHz) δ: 1.055 (s, 3H, C17-H), 1.083 (s, 3H, C19-H), 1.724 (s, 3H, C19-H), 1.858 (m, 1H, C6-βH), 1.913 (s, 3H, $CH_3$-Ph), 2.193 (s, 3H, C10-OC(O)$CH_3$), 2.514 (m, 1H, C6-aH), 3.663 (d, 1H, J=7.0 Hz, C3-H), 4.110 (d, 1H, J=8.5, C20-aH, A of AB), 4.133 (s, 3H, N—$CH_3$), 4.230 (d, 1H, J=8.5, C20-aH, B of AB), 4.315 (dd, 1H, J=8.7, 10.7, C7-H), 4.901 (dd, 1H, J=1.0, 7.7, C5-H), 5.501 (d, 1H, C2-H, J=7.0), 5.702 (bt, 1H, C2'-H, J=8.0), 5.951 (dd, 1H, C13-H, J=1.0, 8.0), 6.120 (bd, 1H, C3'-H, J=10.0), 6.181 (s, 1H, C10-H) 7.702 (t, 1H, N—H, J=7.5), 7.33–7.45 (m, 8H, Ar—H), 7.56–7.62 (m, 4H, Ar—H), 7.56–7.62 (m, 4H, Ar—H), 7.68–7.75 (m, 4H, Ar—H), 8.00–8.05 (m, 1H Ar—H), 8.23–8.28 (m, 1H, Pyr-H), 8.41 (m, 1H, Pyr-H). IR (neat, KCl plate) $cm^{-1}$: 3640–3120 (bm), 3030–2870 (bm), 2320 (m), 1720 (s), 1630 (m), 1560 (m), 1500 (m), 1360 (s), 1160 (m), 1070 (m), 700 (m). UV/Vis ($CHCl_3$) nm: 254, 280. FAB HRMS: calc for $C_{53}H_{57}O_{14}N_2$: 945.3810; found: 945.3810.

The molecular structures of taxol and of taxol-2'-MPT are illustrated in Scheme 3A. The synthesis of taxol-2'-MPT is illustrated in Scheme 3B.

Synthesis of Taxol-7-MPT

The synthesis of taxol-7-MPT differed only slightly from the synthesis of Taxol-2'-MPT. Taxol (10 mg, 0.012 mM), from NaPro Biochemicals, Boulder, Colo., USA, was dissolved in methylene chloride (2.0 mL) and treated sequentially with triethylamine (67 microL, 0.48 mM, 40 equivalents) and 2-fluoro-1-methylpyridinium tosylate (34 mg, 0.12 mM, 10 equivalents) Aldrich Chemicals, and allowed to stir at ambient temperature for 5 minutes. Purification via reverse phase high pressure liquid chromatography (HPLC) gave pure taxol-2'-MPT (12 mg, 93% yield) as a white amorphous solid. The Rf of taxol-7-MPT is about 0.3 minutes less than the Rf of taxol-2'-MPT. The yield was 11 mg or 85%. Spectroscopic data ($^1H$ NMR and HRMS) were as expected.

Synthesis of Taxol-bis-2',7-MPT

The synthesis of taxol-bis-2',7-MPT differed from the synthesis of Taxol-7-MPT only with respect to reaction time. Taxol (10 mg, 0.012 mM), from NaPro Biochemicals, Boulder, Colo., USA, was dissolved in methylene chloride (2.0 mL) and treated sequentially with triethylamine (67 microL, 0.48 mM, 40 equivalents) and 2-fluoro-1-methylpyridinium tosylate (34 mg, 0.12 mM, 10 equivalents) Aldrich Chemicals, and allowed to stir at ambi- ent temperature for 18 hours. Purification via reverse phase high pressure liquid chromatography (HPLC) gave pure taxol-2'-MPT (12 mg, 93% yield) as a white amorphous solid. The Rf of taxol-bis-2',7-MPT is about 0.3 minutes less than the Rf of taxol-2'-MPT. The yield was 13 mg or 85%. Spectroscopic data ($^1$H NMR and HRMS) were as expected.

Alternative synthetic schemes based upon the method of T. Mukaiyama (*Angewandte Chemie* 1979, 18(18), 707–808) using a variety of onium salts of 2-halogenated aza-arenes for derivatizing either the 2' or the 7 positions of taxol are illustrated in the following scheme:

What is claimed is:

1. A taxoid molecule comprising a tricyclic ABC ring skeleton represented by the following structure:

wherein $R_1$ is selected from the group consisting of H, OH, and MPT, $R_4$ is selected from the group consisting of H, OH, and MPT, and $R_3$ is selected from the group consisting of H and MPT, with the proviso that at least one of $R_1$, $R_3$, and $R_4$ is MPT, and where $R_2$ is selected from the group consisting of structures selected from the group represented by the following structures:

* * * * *